(12) United States Patent
Zarinetchi et al.

(10) Patent No.: US 6,389,318 B1
(45) Date of Patent: May 14, 2002

(54) MAGNETIC SHIELD FOR PRIMARY COIL OF TRANSCUTANEOUS ENERGY TRANSFER DEVICE

(75) Inventors: Farhad Zarinetchi, Chelmsford; Stephen J. Keville, Harvard, both of MA (US)

(73) Assignee: Abiomed, Inc., Danvers, MA (US)

( * ) Notice: Subject to any disclaimer, the term of this patent is extended or adjusted under 35 U.S.C. 154(b) by 0 days.

(21) Appl. No.: 09/347,322

(22) Filed: Jul. 2, 1999

Related U.S. Application Data

(63) Continuation-in-part of application No. 09/110,608, filed on Jul. 6, 1998, now Pat. No. 6,324,430.

(51) Int. Cl.[7] .............................................. A61B 18/00
(52) U.S. Cl. .............................. 607/61; 607/63; 607/60
(58) Field of Search .......................... 607/33, 32, 37, 607/36, 60, 61, 65, 63; 600/13, 9, 14, 15

(56) References Cited

U.S. PATENT DOCUMENTS

| | | | |
|---|---|---|---|
| 3,195,540 A | 7/1965 | Waller | 128/422 |
| 3,357,432 A | 12/1967 | Abell | 128/419 |
| 3,824,129 A | 7/1974 | Fagan, Jr. | 136/6 R |
| 3,888,260 A | 6/1975 | Fischell | 128/419 PG |
| 3,934,177 A | 1/1976 | Horbach | 317/100 |
| 3,942,535 A | 3/1976 | Schulman | 128/419 |
| 4,012,769 A | 3/1977 | Edwards et al. | 357/81 |
| 4,041,955 A | 8/1977 | Kelly et al. | 128/419 P |
| 4,068,292 A | 1/1978 | Berry et al. | 361/437 |
| 4,071,032 A | 1/1978 | Schulman | 128/419 P |
| 4,104,701 A | 8/1978 | Baranowski | 361/386 |
| 4,266,533 A * | 5/1981 | Ryaby et al. | 600/14 |
| 4,441,498 A | 4/1984 | Nordling | 128/419 |
| 4,517,585 A | 5/1985 | Ridout et al. | 357/81 |
| 4,539,433 A * | 9/1985 | Ishino et al. | 174/35 MS |
| 4,586,508 A | 5/1986 | Batina et al. | 128/419 |
| 4,665,896 A | 5/1987 | LaForge et al. | 128/1 D |
| 4,679,560 A | 7/1987 | Galbraith | 128/419 |
| 4,741,339 A | 5/1988 | Harrison et al. | 128/419 |
| 4,944,299 A | 7/1990 | Silvian | 128/419 |
| 5,000,178 A | 3/1991 | Griffith | 128/419 |
| 5,214,392 A | 5/1993 | Kobayashi et al. | 330/10 |
| 5,312,439 A | 5/1994 | Loeb | 607/2 |
| 5,324,316 A | 6/1994 | Schulman et al. | 607/61 |
| 5,358,514 A | 10/1994 | Schulman et al. | 607/61 |
| 5,411,537 A | 5/1995 | Munshi et al. | 607/33 |

(List continued on next page.)

FOREIGN PATENT DOCUMENTS

EP      A-0 507 360      10/1992

OTHER PUBLICATIONS

Altieri, F., et al., "Progress Towards a Totally Implantable Artificial Heart" *Cardiovascular Science & Technology: Basic & Applied, I Precised Proceedings*, pp. 213–216 (1989–1990).

(List continued on next page.)

*Primary Examiner*—Kennedy Schaetzle
(74) *Attorney, Agent, or Firm*—Nutter McClennen & Fish LLP

(57) ABSTRACT

A transcutaneous energy transfer device is provided which has a magnetic shield covering the primary winding of the device to reduce sensitivity of the device to conducting objects in the vicinity of the coils and to increase the percentage of magnetic field generated by the primary coil which reaches the secondary coil. This shield is preferably larger than the primary coil in all dimensions and is either formed of a high permeability flexible material, for example a low loss magnetic material in a flexible polymer matrix, with perforations formed in the material sufficient to permit ventilation of the patient's skin situated under the shield, or the shield may be formed of segments of very high permeability material connected by a flexible, porous mesh material.

45 Claims, 4 Drawing Sheets

FOREIGN PATENT DOCUMENTS

| | | | | |
|---|---|---|---|---|
| 5,527,348 A | | 6/1996 | Winkler et al. | 607/30 |
| 5,621,369 A | * | 4/1997 | Gardner et al. | 335/302 |
| 5,740,257 A | | 4/1998 | Marcus | 381/71.6 |
| 5,948,006 A | * | 9/1999 | Mann | 607/61 |
| 5,951,459 A | * | 9/1999 | Blackwell | 600/13 |
| 5,959,522 A | | 9/1999 | Andrews | 336/200 |
| 6,048,601 A | * | 4/2000 | Yahagi et al. | 428/147 |

OTHER PUBLICATIONS

Mitamura, Y., et al., "Development of Transcutaneous Energy Transmission System" *Artificial Heart* 2, pp. 265–271 (1988).

Phillips, R.P., "A High Capacity Transcutaneous Energy Transmission System" *ASAIO Journal*, vol. 41: M259–M262 (1995).

Sutton, G.W., "A Miniaturized Device for Electrical Energy Transmission Through Intact Skin—Concepts and Results of Initial Tests" *Artificial Organs*, vol. 5(A): Abstracts, 2 pages, Paris, (Jul. 8–10, 1981).

Abe et al. "Development of Transcutaneous Energy Transmission System for Totally Implantable Artificial Heart" 1988.

Bearnson et al. "Electronics Development for the Utah Electrohydraulic Total Artificial Heart" 1993.

Callewaert et al. "A Programmable Implantable Stimulator with Percutaneous Optical Control" 1987.

Fraim et al. "Performance of a Tune Ferrite Core Transcutaneous Transformer" 1970.

Galbraith et al. "A Wide–Band Efficient Inductive Transdermal Power and Data Link with Coupling Insensitive Gain" 1987.

Mitamura et al. "A Transcutaneous Optical Information Transmission System for Implantable Motor–drive Artificial Hearts" 1990.

Mitamura et al., "Development of an Implantable Motor–Driven Assist Pump System" 1990.

Mitamura et al. "Development of Motor Driven Assist Pump Systems" 1987.

Mohammed et al. "A Miniature DC–DC Converter for Energy Producing Implantable Devices" 1987.

Mohammed et al. "Design of Radio Frequency Powered Coils for Implantable Stimulators" 1987.

Myers et al. "A Transcutaneous Power Transformer" 1968.

Rintoul et al. "Continuing Development of the Cleveland Clinic–Nimbus Total Artificial Heart" 1993.

Sherman et al. "Transcutaneous Energy Transmission (TET) System for Energy Intensive Prosthetic Devices" 1986.

Weiss et al. "A Telemetry System for the Implanted Total Artificial Heart and Ventricular Assist Device" 1987.

Weiss et al. "Permanent Circulatory Support Systems at the Pennsylvania State University" 1990.

Geselowitz et al. "The Effects of Metals on a Transcutaneous Energy Transmission System" Sep. 1992.

Miller et al. "Development of an Autotuned Transcutaneous Energy Transfer System" 1993.

Mussivand et al. "Transcutaneous Energy Transfer System Performance Evaluation" May 1993.

Sherman et al. "Energy Transmission Across Intact Skin for Powering Artificial Internal Organs" 1981.

International Search Report from PCT application No. PCT/US99/15228, filed June 7, 1999.

Hidetoshi Matsuki et al. "Energy Transferring System Reducing Temperature Rise For Implantable Power Consuming Devices" Proceedings of the 18th Annual Conference of the IEEE Engineering I Medicine and Biology Society, Amsterdam Oct. 31–Nov. 3, 1996, vol. 1, pp. 185/186.

Patent Abstracts of Japan, vol. 199, No. 505, Jun. 30, 1995 & JP 07 046164 A (Tokin Corp.) Feb. 14, 1995.

* cited by examiner

MAGNETIC SHIELD FOR PRIMARY COIL OF TRANSCUTANEOUS ENERGY TRANSFER DEVICE

RELATED APPLICATION

This application is a continuation-in-part of U.S. patent application Ser. No. 09/110,608 filed Jul. 6, 1998 entitled "MAGNETIC SHIELD FOR PRIMARY COIL OF TRANSCUTANEOUS ENERGY TRANSFER DEVICE," and naming as inventors Fred Zarinetchi and Steven J. Keville, now U.S. Pat. No. 6,324,430.

The following commonly-owned application is related to the present application and its disclosure is incorporated by reference in the present application:

U.S. patent application Ser. No. 09/110,607, filed Jul. 6, 1998, entitled "TET WITH MAGNETIC FIELD PROTECTED COMPONENTS IN SECONDARY COIL," naming as inventors Fred Zarinetchi and Robert M. Hart, and now abandoned.

FIELD OF THE INVENTION

This invention relates to transcutaneous energy transfer (TET) devices and, more particularly, to an improved primary coil for such device which reduces sensitivity to conductive objects in proximity of the TET.

BACKGROUND OF THE INVENTION

Many medical devices are now designed to be implantable, including pacemakers, defibrillators, circulatory assist devices, cardiac replacement devices such as artificial hearts, cochlea implants, neuromuscular simulators, biosensors, and the like. Since almost all of the active devices (i.e., those that perform work) and many of the passive devices (i.e., those that do not perform work) require a source of power, inductively coupled transcutaneous energy transfer (TET) devices and information transmission systems for such devices are coming into increasing use.

These systems generally include an external primary coil and an implanted secondary coil, separated by an intervening layer of tissue. This design generally results in a loosely-coupled transformer with no magnetic shielding. Therefore, transformer parameters, such as mutual and self-inductance values, and the effective series resistance of each coil, can be altered by the presence of conductive objects, for example a metal plate, in the vicinity of the primary coil. Such parameter changes can result in undesired, and in some cases potentially catastrophic, variations in power delivered to the implanted device. Further, an unshielded primary coil generates a magnetic field which is directed in substantially equal parts toward the secondary coil, where it performs useful work, and away from the secondary coil where the magnetic field energy is substantially wasted. If a higher percentage of the magnetic field from the primary coil could be directed to the implanted secondary coil, the energy required to drive the TET device could be reduced. This could result in the device being driveable from a lower energy, and thus a smaller, lighter and less expensive source, or less drainage on could result in an existing source, facilitating longer battery life between replacement or recharging.

A need therefore exists for an improved primary coil construction for a TET device which both reduces sensitivity of the device to conducting objects in the vicinity of the coils and, preferably, which increases the percentage of magnetic field generated by the primary coil which reaches the secondary coil. Such a device and method would significantly enhance the energy transfer efficiency of the TET device.

SUMMARY OF THE INVENTION

In accordance with the above, this invention provides a transcutaneous energy transfer device having an external primary coil to which energy to be transferred is applied and an implanted secondary coil inductively coupled to the primary coil and connected to apply energy to a subcutaneous utilization device, the invention being characterized by the inclusion of a magnetic shield covering the primary winding. The shape of the shield is generally substantially the same as that of the primary coil, but the size of the shield should be greater than that of the primary coil. More particularly, to fully reflect magnetic field toward the secondary coil, the shield should overlap the primary coil on all sides by at least the thickness (t) of the shield. Where the primary coil has a generally circular shape with a diameter d, the shield has a generally circular shape with a diameter D, where D>d and preferably $D \geq d+2t$. The thickness of the shield for a circular shield is preferably much greater than $D/\mu$ where $\mu$ is the magnetic permeability relative to free space of the shield material, or more generally, $t >> X\mu$, where X is a major dimension of the shield.

The shield normally has a plurality of ventilation perforations formed therein which perforations are preferably formed parallel to the magnetic field direction so that the path taken through the material of the shield is as short as possible. For embodiments where the primary coil is circular, the perforations are a plurality of radial slots, which slots are slightly wedge-shaped for an illustrative embodiment. To assure adequate ventilation, the perforations should make up between approximately 25% and 75% of the shield area. Since the perforations reduce $\mu$ of the shield material, for the shield thickness to continue to satisfy $t >> X\mu$, t needs to increase proportionally (i.e., if the shield is 50% perforated, shield thickness $t_p=2t$). Perforation size should also be small compared the smallest coil in the TET device.

The shield should also be flexible so as to be able to conform to the contours of a patient's body. To achieve this flexibility, for one embodiment of the invention the shield is formed of a low loss magnetic material in a flexible polymer matrix, the shield being formed of a ferrite powder in a silicon rubber for an illustrative embodiment. For another embodiment, the shield is formed of a plurality of segments of a very high permeability material connected by a porous, flexible material. To the extent there are spacings between adjacent segments in a direction substantially perpendicular to the primary coil magnetic field in order to enhance flexibility, such spacings are much smaller than spacings in a direction parallel to the magnetic field.

The shield is also dimensioned and formed of a material which reflects most of the magnetic field directed away from the secondary coil back toward the secondary coil. This significantly enhances the efficiency of energy transfer across the skin boundary by the TET device.

In one embodiment the segments include a plurality of segments arranged in one or more concentric rings, each said concentric ring including segments of substantially the same size. In another embodiment, the plurality of segments are constructed and arranged so as to form a gap between radially opposing segments in said ring. In this embodiment, the segments further include a center disk shaped to fit within said gap.

In anther aspect of the invention, the shield and said primary coil are mounted together to form a primary coil assembly. A substantially impervious coating is applied to the assembly to make it substantially waterproof and easy to clean. In one particular embodiment, the primary coil assembly is vinyl dip coated.

In another aspect of the invention, the primary coil is operationally decoupled from a drive circuit prior to physical disconnection of electrical contacts through which current is transferred from the drive circuitry to said primary coil. The physical connection of electrical contacts through which current is transferred from the drive circuitry to said primary coil occurs prior to operationally coupled the primary winding to the drive circuit. In one implementation, the primary coil is electrically coupled to the drive circuit via an electrical connector. The electrical connector includes power transfer contacts and anti-arcing contacts. The anti-arcing contacts electrically mate after and break before said power transfer contacts, and are electrically connected to control circuitry operationally interposed between the drive circuit from the primary winding. In one embodiment, the control circuitry is located in said drive circuitry while in another embodiment, it is located in the connector.

Further features and advantages of the present invention as well as the structure and operation of various embodiments of the present invention are described in detail below with reference to the accompanying drawings. In the drawings, like reference numerals indicate like or functionally similar elements. Additionally, the left-most one or two digits of a reference numeral identifies the drawing in which the reference numeral first appears.

BRIEF DESCRIPTION OF THE DRAWINGS

This invention is pointed out with particularity in the appended claims. The above and further advantages of this invention may be better understood by referring to the following description when taken in conjunction with the accompanying drawings, in which:

DETAILED DESCRIPTION

Figure 1:
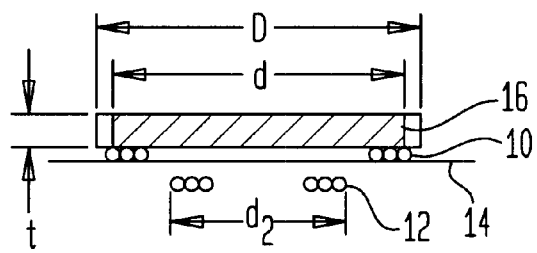
FIG. 1 is a side cutaway view of a TET coil pair with a magnetically shielded primary coil in accordance with the teachings of this invention.

FIG. 1 shows a primary coil 10 having a diameter d and a secondary coil 12 having a diameter $d_2$, where $d_2<d$, of a TET device for transferring energy through a skin boundary 14. As indicated previously, such a standard TET device has at least two shortcomings. First, the magnetic field of primary coil 10 normally generates substantially equal magnetic fields in directions both toward and away from secondary coil 12. This means that a conductive object in the vicinity of primary coil 10, and in particular a conductive object passing through the magnetic field of this coil, can alter parameters of the coil such as its self-inductance values and effective series resistance, thus resulting in a variation in the energy transferred to secondary coil 12. Since it is desired that this energy transfer be substantially uniform, the potential for spurious variations in energy transfer is at best undesirable, and at worst can have potentially catastrophic consequences for the patient.

A second problem is that energy is required to generate the magnetic field in the direction away from the secondary coil and, since this magnetic field does not contribute to the energy transfer, device efficiency is reduced. Stated another way, the fact that half the magnetic field generated by the primary coil is not being utilized for energy transfer substantially increases the amount of energy which must be applied to the primary coil in order to achieve a desired energy level at the secondary coil.

Aspects of the present invention overcome these problems by providing a magnetic shield 16 mounted over primary windings 10. The shape of shield 16 is preferably substantially the same as that of primary coil 10, although this is by no means a limitation on the invention. The size of the shield is also preferably greater than that of the primary winding. Thus, in FIG. 1 it is assumed that both primary winding 10 and shield 16 have a generally circular shape, with the diameter D of the shield shown as being greater than the diameter d of the coil. More specifically, to fully reflect magnetic field toward the secondary coil, shield 16 should overlap primary coil 10 on all sides by at least the thickness (t) of the shield. Thus, for a circular shield, it is preferable that $D \geq d+2t$. For a non-circular coil, having various dimensions xi, the corresponding dimension for the shield would in each instance be $X_i \geq x_i + 2t$.

The thickness (t) of shield 16 should be much greater than $X/\mu_r$ where $\mu_r$ is the magnetic permeability of the magnetic shield material relative to free space and X is a major dimension of the shield. Therefore, for the circular shield of the figures, $t>>D/\mu_r$. For an illustrative embodiment, D=5.5", d=5", t=0.25" and $\mu_r$ is approximately 100. However, the dimensions of the shield will vary significantly depending on the application.

Shield 16 is preferably formed of a low loss magnetic material. This results in the magnetic field emanating from primary coil 10 in the direction of shield 16 being substantially reflected with minimum absorption by shield 16, back toward secondary coil 12. With $D \geq d+2t$, substantially all of the magnetic field from the primary coil can be either directed or reflected to the secondary coil 12, substantially increasing the transfer efficiency of the TET device, this efficiency theoretically being substantially doubled.

While in FIG. 1 the skin surface 14 is shown as being substantially flat, as a practical matter, the skin surface in most applications of this invention will be curved in various ways, requiring that shield 16 be flexible so as to be able to conform to the contours of the skin surface in the transfer area. The material for shield 16 is therefore preferably a low loss magnetic material in a flexible polymer matrix. For one illustrative embodiment of the invention, ferrite powder (Steward MnZn loading powder #73300) is embedded in a silicone rubber in a ratio by weight of 9 parts silicone to 12 parts ferrite powder. Since the polymer in which the magnetic material is embedded significantly reduces the magnetic permeability of the material (the reduction being by a factor of 10 for the illustrative composition), it is desirable incorporate as much ferrite powder as possible while retaining the required flexibility of the shield.

Figure 2:
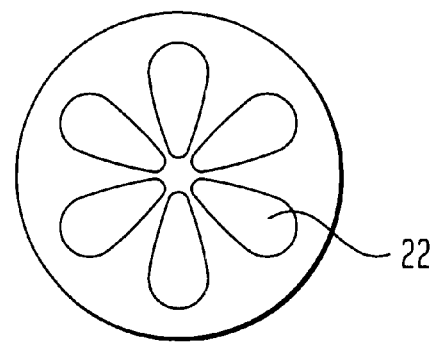
FIG. 2 is a top view of a shield shown in FIG. 1 for one embodiment of the invention.
Figure 3:
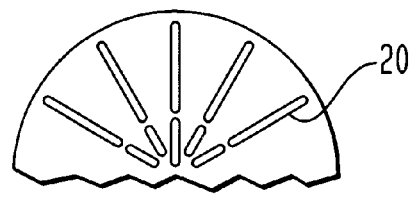
FIGS. 3 and 4 are partial top views of the shield shown in FIG. 1 for two alternative embodiments of the invention.
Figure 4:
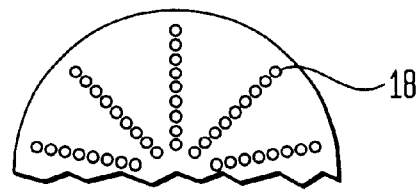

Since the TET device may remain in place for a substantial period of time, it is important that the skin of the patient under shield 16 be able to "breathe", or in other words that air be allowed access to this skin, in order to prevent skin degeneration. It is therefore important that perforation holes be provided in shield 16. Since any openings in the shield may permit potential magnetic field leakage above the shield, the perforations are preferably parallel to the magnetic field in order to minimize magnetic flux paths through the shield material, thus enhancing reflection and minimizing leakage. For the embodiments of FIGS. 2–4 wherein shield 16 is substantially circular, to achieve this objective, the perforations are implemented in a substantially radial manner, as shown. With other primary coil shapes, the perforation pattern may very well be different. The smaller and thinner the perforations, the less potential there is for magnetic field leakage, so that the arrangement shown in FIG. 4, with a radially arranged series of small holes 18 is preferable from a shielding standpoint. However, the arrangement of FIG. 4 may not provide sufficient ventilation for long-term usage. Alternatively, an arrangement such as that shown in FIG. 3, with radial slots 20 which are relatively thin to the magnetic field path so as to preventing significantly magnetic field leakage, while still providing reasonable ventilation. More specifically, it has been found that, in order to achieve adequate ventilation, the perforations should make up between 25% and 75% of the area of the shield, with perforations comprising approximately 50% of the area of the shield being generally preferred for long-term usage. This may require a configuration such as that shown in FIG. 2, with generally radially-arranged, wedge-shaped slots 22 to increase the perforation area. However, since the perforations reduce $\mu_r$ for this shield from what it would be without the perforation. The amount of such a reduction is generally in direct proportion to the percentage of the surface area of the shield absorbed by such perforations. This, in combination with the above-noted objective that $t>>D/\mu_r$, the thickness t should generally be increased is some relationship with the increase in surface area dedicated to the perforations. For example, in one embodiment wherein the perforations comprise 50% of the shield area, the shield thickness $t_p$ has been increased such that $t_p=2t$. Other linear and non-linear relationships between shield thickness and surface area absorbed by the perforations.

In one aspect of the invention, a limitation on perforation size is that the perforation size is small compared to the size of the smallest coil in the TET device. Referring to the device of FIG. 1, for example, the size of the individual perforations are much smaller than that of secondary coil 12. For example, if the diameter $d_2$ of the secondary coil is roughly 1.5 inches, the perforations should be less than approximately 33% of the diameter $d_2$ or 0.5 inches in their smallest dimension. In other embodiments, the smallest dimension of the perforations is preferably less than approximately 20% of the diameter $d_2$; in other embodiments, the smallest dimension of the perforations is between approximately 20–60% of the diameter $d_2$. While shield thickness as well as size and shape of the perforations may be adjusted to minimize magnetic field leakage through shield 16, and thus to minimize the interference or loss of energy transfer efficiency caused by a conducting object near or in contact with the shield, it is desirable in any event that the perforations not result in a decrease in coupling efficiency of greater than 20%, and preferably less than 16%, when a conducting object is brought in close proximity of the shield.

Figure 5:
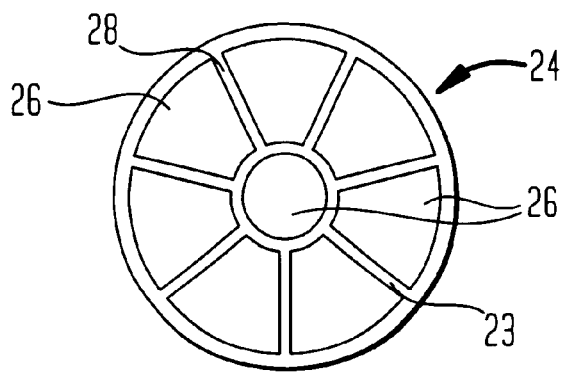
FIG. 5 is a top view of still another embodiment of the invention.

FIG. 5 illustrates a shield 24 which differs from the shields 16 previously discussed in that, instead of being formed of a piece of flexible material having perforations or openings 18–22 formed therein, the shield is formed of segments 26 of a very high permeability but inflexible material, such as a hard ferrite, which segments are connected to each other with a breathable and porous mesh 28 of a polymer or other flexible material. Since the effective $\mu_r$ of the segments 26 is much higher than that of the material used in the flexible shield 16, the shield may be made substantially thinner than for the prior embodiments while still satisfying the requirement that $t>>D/\mu_r$. Thus, a thickness in the order of ⅛ inch or less for shield 24 might be possible, making the shield much more comfortable for the wearer. Further, the high $\mu_r$ segments 26 permit a larger percentage of the area of the shield to be covered by mesh 28 while still achieving desired shielding, enhancing breathability and protecting against skin degeneration. Segments 26 may take up 25–75% of the shield area, but would typically take up 50% or less of such area. The radial spacings between segments would, as previously indicated, have a smallest dimension less than the diameter of the secondary coil, and might, for example be 0.5 inches for a roughly 1.5 inch secondary coil. However, the circular spacing, which is required to obtain flexibility in all dimensions for the shield, which spacing is perpendicular to the magnetic field of coil 10, should be much thinner, and for the dimensions above would typically be approximately 0.1 inches. For many applications, the embodiment shown in FIG. 5 may be the preferred embodiment.

Figure 6A:
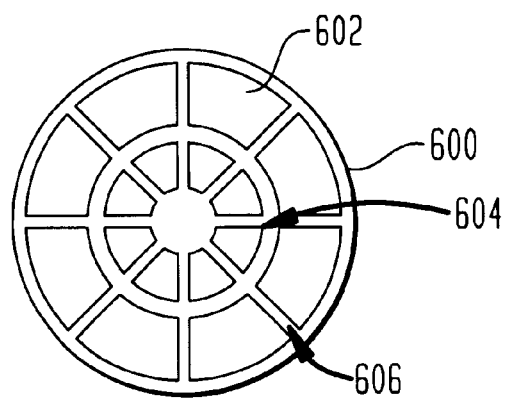
FIG. 6A is an alternative embodiment of a shield having a tiled ferrite design.

FIG. 6A is an alternative embodiment of a shield having a tiled ferrite design. In this embodiment, shield 600 includes multiple concentric rows of segments 602. Segments 602 in inner concentric row 604 are small relative to segments 602 in outer concentric row 606. In should be understood that any number of concentric rows may be implemented.

Figure 6B:
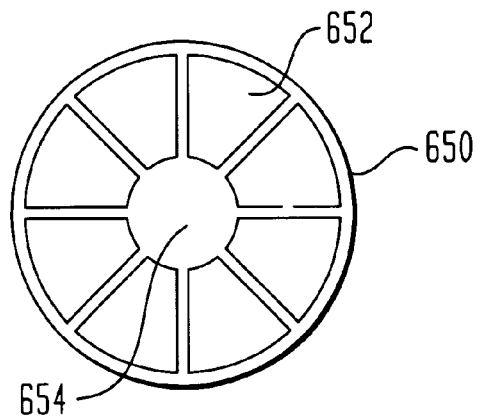
FIG. 6B is another alternative embodiment a shield having a tiled ferrite design.

FIG. 6B is a further an alternative embodiment a shield having a tiled ferrite design. In this embodiment, shield 650 includes multiple concentric rows of segments 652 similar to segments 26 in shield 24 shown in FIG. 5. However, in this embodiment, the center disk segment is omitted. The large open space 654 in the center of the shield 650 aligned approximately with the center of the primary coil reduces minimally the coupling efficiency of the device while improving the skin ventilation under the primary coil. It should be understood that the size of the center space 654 may have any dimensions suitable for a desired coupling efficiency.

Figure 7A:
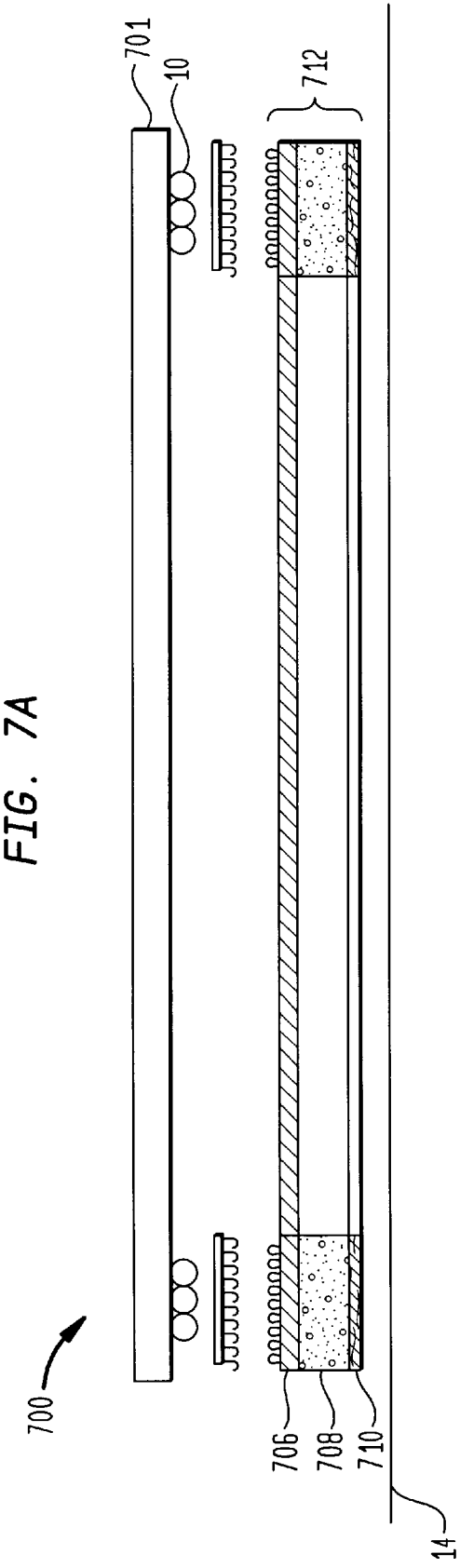
FIG. 7A is a cross-sectional view of one embodiment of a primary coil assembly that is providing a comfortable interface between the TET Primary coil and skin.

FIG. 7A is a cross-sectional view of one embodiment of a primary coil assembly 700 that is configured to provide a comfortable interface between the TET Primary coil 10 and skin 14 with a low-cost, disposable part that can easily be removed and replaced. Primary coil assembly 700 includes primary coil 10 and ferrite shield 16, as described above. To prevent adverse effects due to having such a rigid device continually against a same region of the skin 14, primary coil assembly 700 is a compliant skin-compatible cushion 702. Cushion 702 is preferably ventilated to relieve perspiration and provide for cooling of the skin 14. In addition cushion 702 is preferably disposable so that it can easily be removed and replaced when it becomes soiled.

Referring to FIG. 7A, one embodiment of cushion 702 is illustrated. A hook and loop fastening material 704 such as VELCRO is fastened to the side of primary coil 10 opposite shield 701, schematically shown in FIG. 7A. This provides for the easily attachment and detachment of cushion 702. Cushion 702 includes 3 layers in the illustrative embodiment. A VELCRO loop material 706 adapted to be attached to VELCRO hook material 704. An open cell foam material 708 for providing compliance and breathability is bonded to loop material 706. A skin-compatible material 710 such as terry-cloth is bonded to open cell foam layer 708 to provide a ventilated, non-allergenic, non-irritating skin contacting surface. The above construction enables cushion 702 be formed from a low-cost, die-cut part.

Figure 7B:
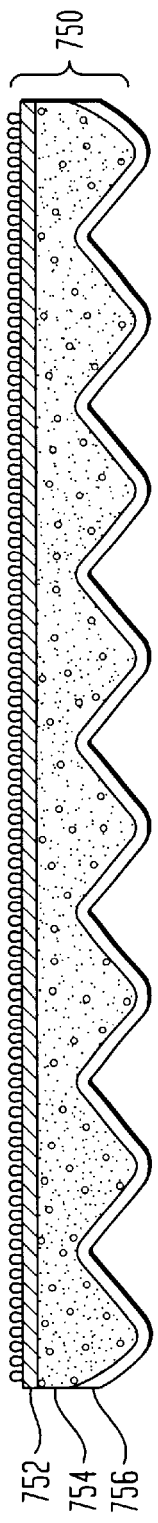
FIG. 7B is an alternative embodiment of the cushion illustrated in FIG. 7A.

FIG. 7B is an alternative embodiment of the cushion according to this aspect of the present invention. In this embodiment, a cushion 750 is a laminate similar in construction to cushion 712. In this embodiment, however, the open cell material 708 is crenellated to provide increased ventilation between the cushion surface and the skin 14. The skin-compatible layer 756 is bonded to open cell foam layer 654 and, therefore, follows crenelate surface of foam layer 754. It should be understood that other well-known materials may be used. For example, skin-contact material 756 may be constructed so as to serve as a wick to draw perspiration from the skin.

In alternative embodiments, the shield and primary coil 10 are mounted together is some known manner and a impervious coating is applied to make the shield and TET primary coil more durable, waterproof, and washable. In one particular embodiment, for example, vinyl dip coating is used.

Figure 8:
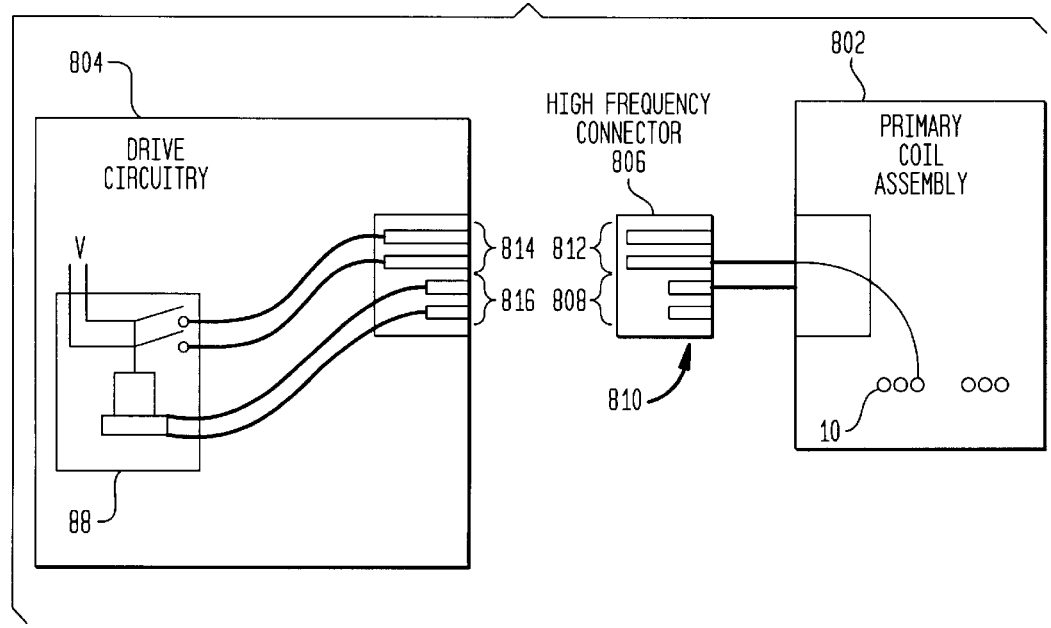
FIG. 8 is a schematic block diagram of a connector for electrically connecting a drive circuit with the primary coil in accordance with one embodiment of the present invention.

FIG. 8 is a schematic block diagram of another aspect of the present invention. In this aspect of the invention, a primary coil assembly 802 is detachable from drive electronics 804 that control the primary coil 10 within the primary coil assembly 802. To avoid degradation of the high current connector as a result of arching during live connecting/disconnection of the primary coil assembly 802 and drive circuitry 804, the drive circuitry 804 is automatically disabled before disconnecting power transfer contacts for the primary coil 10, and automatically enabled only after connecting the power transfer contacts for the primary coil 10.

In the illustrative embodiment illustrated in FIG. 8, for example, a spare separate set 808 of contacts 810 in the connector 806 are constructed and arranged to mate last and break first relative to the one or more contacts 812 that provide power to primary coil 10. The anti-arching contacts 808 are connected to well-known circuitry 818 that enables or disables the drive circuitry 804, shown schematically as a relay interposed between a voltage source and receiving power transfer contacts 814. In particular, in order to mate last and break first, the anti-arching contacts 808 in connector 806 have a length that is shorter than the power transfer contacts 812. In addition, receiving power transfer contacts 814 that receive contacts 812 are longer than receiving anti-arching contacts 816 that receive anti-arching contacts 808. This embodiment, therefore, enables the TET drive circuitry 804 to be automatically disabled before disconnecting the power transfer contacts for the primary coil 10 while automatically turning on the primary coil 10 after reconnection of the coil power transfer contacts 812 and 814. It should be understood that other schemes may be implemented to perform this function. For example, a latches may be used to connect male and female portions of a high frequency connector coupling drive circuitry 804 and primary coil assembly 802. The latch would be electrically connected to well-known circuitry that would enable or disable the drive circuitry similar to that described above. Operation of the latch to disconnect the two connector halves would cause the drive circuitry 804 to be disabled and the power through contacts 812 to be removed prior to when the contacts 812 are physically disconnected from the receiving contacts 814. Similarly, contacts 812 would first come into physical contact with receiving contacts 814 before anti-arching contacts 810 come into contact with corresponding receiving contacts 816. This subsequent contact would cause automatically the drive circuitry 804 to become operational allowing power to travel through contacts 812. It should also be understood that virtually any other type of electrical circuit switch or other on/off device may be used to operationally disconnect primary coil 10 and drive circuitry 804 prior to the decoupling of the contacts 812 and 814 and operationally connecting primary coil 10 and drive circuitry 804 after the connection of contacts 812 and 814.

It should also be understood that control circuitry 818 may be located in drive circuitry 804, primary coil assembly 802 or connector 806, depending on the application.

Such automatic connect/disconnect feature allows for greater flexibility. For example, the primary coil 10 may be sterilized easily for use during implant surgery. In addition, it would also allow the patient to wear just the TET primary coil assembly without all of the battery powered electronics, as well as to plug the primary coil into power sources located at convenient places in the home or work environment. Further, separation of the drive circuitry 804 eliminates the weight of the patient-carried electronics and battery pack. This is important, for example, for patients who are physically very weakened.

While the invention has been particularly shown and described above with reference to several preferred embodiments and variations thereon, it is to be understood that additional variations could be made in the invention by those skilled in the art while still remaining within the spirit and scope of the invention, and that the invention is intended to include any such variations, being limited only by the scope of the appended claims.

Further information is described in currently pending U.S. patent application Ser. No. 09/110,608 filed Jul. 6, 1998 entitled "MAGNETIC SHIELD FOR PRIMARY COIL OF TRANSCUTANEOUS ENERGY TRANSFER DEVICE," and naming as inventors Fred Zarinetchi and Steven J. Keville, now currently pending, incorporated herein by reference in its entirety.

What is claimed is:

1. A transcutaneous energy transfer device comprising:
   an external primary coil to which energy to be transferred is applied;
   an implanted secondary coil configured to be inductively coupled to the primary coil and connected to apply energy to a subcutaneous utilization device; and
   a magnetic shield covering a side of the primary coil opposite the secondary coil, wherein the magnetic shield comprises a plurality of segments of very high permeability material arranged in one or more concentric rings and connected by a porous flexible material.

2. The device of claim 1, wherein each concentric ring including elements of the same size.

3. The device of claim 1, wherein the plurality of segments are constructed and arranged to provide a gap within an innermost concentric circle and wherein the magnetic shield further comprises a center disk shaped to fit within the gap.

4. The device of claim 1, wherein spacings between adjacent segments in a direction substantially parallel to the magnetic field direction of the primary coil are less than the dimensions of the smallest coil in the device, and spacings between adjacent segments in a direction substantially perpendicular to the magnetic field direction are much less than the spacing in said parallel direction.

5. The device of claim 1, wherein the segments cover approximately 25% to 75% of an area occupied by the shield.

6. The device of claim 1, wherein said shield is larger than said primary coil.

7. The device of claim 1, wherein said primary coil has a selected shape and size, and wherein said shield is of substantially the same shape as said primary coil, but of greater size.

8. The device of claim 7, wherein said primary coil has a generally circular shape with a diameter d, and wherein said shield has a generally circular shape with a diameter D, where D>d.

9. The device of claim 8, wherein said shield has a thickness t, and wherein D≧d+2t.

10. The device of claim 8, wherein the shield is formed of a material having a magnetic permeability relative to free space ($\mu_r$) and has a thickness (t), where t>>D/$\mu_r$.

11. The device of claim 1, wherein the shield is formed of a material having a magnetic permeability relative to free space ($\mu_r$), has a major dimension X, and has a thickness (t) where t>>X/$\mu_r$.

12. The device of claim 1, wherein said primary coil generates a magnetic field which is directed both toward and away from said secondary coil and wherein said shield is dimensioned and is formed of a material which reflects most of the magnetic field directed thereto toward said secondary coil.

13. A transcutaneous energy transfer device comprising:
an external primary coil to which energy to be transferred is applied;
a drive circuit operationally coupleable to the primary coil;
a connector having a connectable electrical contact element for coupling the primary coil to the drive circuit;
an implanted secondary coil configured to be inductively coupled to the primary coil and connected to apply energy to a subcutaneous utilization device; and
a magnetic shield covering a side of the primary coil opposite the secondary coil;
wherein the primary coil is operationally decoupled from the drive circuit prior to disconnection of the electrical contact element, and wherein connection of electrical contact element occurs prior to operational coupling of the primary coil to the drive circuit.

14. The device of claim 13, further comprising a control circuit operationally interposed between the drive circuit and the primary coil, wherein the electrical contact element includes power transfer contacts and anti-arcing contacts, and wherein the anti-arcing contacts electrically mate after, and break before, the power transfer contacts upon connection and disconnection of the connector and the anti-arcing contacts are electrically connected to the control circuit for coupling and uncoupling the drive circuit to the primary coil upon mating and breaking of the anti-arcing contacts.

15. The device of claim 14, wherein the control circuit is located in the drive circuit.

16. The device of claim 15, wherein the control circuit is located in the connector.

17. A transcutaneous energy transfer device comprising:
an external primary coil to which energy to be transferred is applied;
an implanted secondary coil configured to be inductively coupled to the primary coil and connected to apply energy to a subcutaneous utilization device;
a magnetic shield covering a side of the primary coil opposite the secondary coil; and
a compliant cushion disposed on a side of the primary coil facing the secondary coil;
wherein the cushion is releasably mated to the primary coil.

18. The device of claim 17, wherein the cushion is ventilated.

19. The device of claim 18, wherein the ventilated cushion is adapted to wick perspiration from a patient's skin.

20. The device of claim 18, wherein the cushion comprises an open cell foam layer.

21. The device of claim 20, wherein the cushion comprises a skin-compatible material bonded to the open cell foam layer and adapted to provide a ventilated, non-allergenic, nonirritating skin contacting surface.

22. The device of claim 18, wherein the cushion comprises a skin-compatible material adapted to provide a ventilated, non-allergenic, non-irritating skin contacting surface.

23. The device of claim 17, wherein the cushion is releasably mated to the primary coil by a hook and loop connector.

24. The device of claim 17, wherein the shield is larger than the primary coil.

25. The device of claim 24, wherein the primary coil has a selected shape and size, and wherein the shield is of substantially the same shape as the primary coil, but of greater size.

26. The device of claim 25, wherein the primary coil has dimensions $x_i$ in direction i, wherein the shield has a thickness t and wherein the dimensions of the shield in direction i is $X_i \geq x_i+2t$.

27. The device of claim 25, wherein the primary coil has a generally circular shape with a diameter d, and wherein the shield has a generally circular shape with a diameter D, where D>d.

28. The device of claim 27, wherein the shield has a thickness t, and wherein D≧d+2t.

29. The device of claim 27, wherein the shield is formed of a material having a magnetic permeability relative to free space ($\mu_r$) and has a thickness (t), where t>>D/$\mu_r$.

30. The device of claim 17, wherein the shield is formed of a material having a magnetic permeability relative to free space ($\mu_r$), has a major dimension X, and has a thickness (t) where t)>>X/$\mu_r$.

31. The device of claim 17, wherein the shield has a plurality of ventilation perforations formed therein.

32. A transcutaneous energy transfer device comprising:
an external primary coil to which energy to be transferred is applied;
an implanted secondary coil configured to be inductively coupled to the primary coil and connected to apply energy to a subcutaneous utilization device;
a magnetic shield covering a side of the primary coil opposite the secondary coil; and a compliant cushion disposed on a side of the primary coil facing the secondary coil; wherein the cushion is crenellated.

33. A transcutaneous energy transfer device comprising:

an external primary coil to which energy to be transferred is applied;

an implanted secondary coil configured to be inductively coupled to the primary coil and connected to apply energy to a subcutaneous utilization device;

a magnetic shield covering a side of the primary coil opposite the secondary coil; and a compliant cushion disposed on a side of the primary coil facing the secondary coil;

wherein the cushion is ventilated and the shield has a plurality of ventilation perforations formed therein.

34. The device of claim 33, wherein the perforations are formed parallel to the magnetic field direction.

35. The device of claim 34, wherein the primary coil is substantially circular, and wherein the perforations are a plurality of radial slots.

36. The device of claim 33, wherein the perforations cover approximately 25% to 75% of the area of the shield.

37. The device of claim 36, wherein the perforations cover approximately 50% of the area of the shield.

38. The device of claim 36, wherein all dimensions for the perforations are less than the dimensions of the smallest coil in the device.

39. The device of claim 33, wherein said primary coil has a generally circular shape with a diameter d, and wherein said shield has a generally circular shape with a diameter D, a thickness (t) and is formed of a material having a magnetic permeability relative to free space ($\mu_r$), wherein the perforations result in a reduction $\mu_r$ for the shield which is roughly proportional to the percentage of perforation area, and wherein the shield thickness is increased so as to maintain the relationship $t \gg D\mu_r$.

40. The device of claim 33, wherein the shield is formed of a plurality of segments of a very high permeability material connected by a porous, flexible material.

41. The device of claim 40, wherein spacings between adjacent segments in a direction substantially parallel to the magnetic field direction of the primary coil are less than the dimensions of the smallest coil in the device, and spacings between adjacent segments in a direction substantially perpendicular to the magnetic field direction are much less than the spacing in said parallel direction.

42. The device of claim 40, wherein the segments cover approximately 25% to 75% of said shield area.

43. A transcutaneous energy transfer device comprising:

an external primary coil to which energy to be transferred is applied;

an implanted secondary coil configured to be inductively coupled to the primary coil and connected to apply energy to a subcutaneous utilization device;

a magnetic shield covering a side of the primary coil opposite the secondary coil; and a compliant cushion disposed on a side of the primary coil facing the secondary coil;

wherein the shield is flexible so as to be able to conform to the contours of a patient's body.

44. The device of claim 43, wherein the shield is formed of a low loss magnetic material in a flexible polymer matrix.

45. The device of claim 44, wherein the shield is formed of a ferrite powder in a silicone rubber.

* * * * *